United States Patent [19]

Slate

[11] Patent Number: 4,791,931

[45] Date of Patent: Dec. 20, 1988

[54] DEMAND PACEMAKER USING AN ARTIFICIAL BARORECEPTOR REFLEX

[75] Inventor: John B. Slate, Los Angeles, Calif.

[73] Assignee: Pacesetter Infusion, Ltd., Sylmar, Calif.

[21] Appl. No.: 85,421

[22] Filed: Aug. 13, 1987

[51] Int. Cl.$^4$ ............................................. A61N 1/36
[52] U.S. Cl. ............................................. 128/419 PG
[58] Field of Search ................................ 128/419 PG

[56] References Cited

U.S. PATENT DOCUMENTS

| | | | |
|---|---|---|---|
| 3,358,690 | 12/1967 | Cohen | 128/419 |
| 3,593,718 | 7/1971 | Krasner | 128/419 P |
| 3,638,656 | 2/1972 | Grandjean et al. | 128/419 P |
| 3,650,277 | 3/1972 | Sjostrand et al. | 128/419 C |
| 3,857,399 | 12/1974 | Zacouto | 128/419 P |
| 3,893,452 | 7/1975 | Birnbaum | 128/205 A |
| 3,938,506 | 2/1976 | Birnbaum | 128/205 A |
| 3,996,926 | 12/1976 | Birnbaum | 128/205 A |
| 4,009,721 | 3/1977 | Alcidi | 128/419 PG |
| 4,052,991 | 10/1977 | Zacouto | 128/419 PG |
| 4,140,132 | 2/1979 | Dahl | 128/419 PG |
| 4,201,219 | 5/1980 | Gonzalez | 128/419 PG |
| 4,228,803 | 10/1980 | Rickards | 128/419 PG |
| 4,313,442 | 2/1982 | Knudson et al. | 128/419 PG |
| 4,428,378 | 1/1984 | Anderson et al. | 128/419 PG |
| 4,467,807 | 8/1984 | Bornzin | 128/419 PG |
| 4,566,456 | 1/1986 | Koning et al. | 128/419 PG |
| 4,567,892 | 2/1986 | Plicchi et al. | 128/419 PG |
| 4,600,017 | 7/1986 | Schroeppel | 128/784 |
| 4,644,954 | 2/1987 | Wittkampf et al. | 128/419 PG |
| 4,702,253 | 10/1987 | Nappholz et al. | 128/419 PG |
| 4,719,921 | 1/1988 | Chirite | 128/419 PG |

OTHER PUBLICATIONS

Cohen, Todd, "A theoretical Right Atrial Pressure Feedback Heart Rate Control System to Restore Physiologic Control to the Rate-limited Heart", Jul.-Aug., 1984, pp. 671-677.

Principles of Exercise Responsive Pacemakers, Fearnot et al, IEEE Engineering in Medicine & Biology, v. 3, No. 2, Jun. 1984.

Comparison of the reflext heart rate response to rising and falling atrial pressure in Man, Pickering et al., Cardiovascular Research, 1972, 6, pp. 277-283.

Best & Taylor's Physiological Basis of Medical Practice, John B. West, Editor, 11th Edition, 1985, Chapter 16.

Primary Examiner—Edward M. Coven
Assistant Examiner—Timothy Keegan
Attorney, Agent, or Firm—Leslie S. Miller

[57] ABSTRACT

A device for use in conjunction with a pulse generator is disclosed which provides a variable pulsing rate in response to short term variations in arterial blood pressure, like the baroreceptor system of the healthy body's cardiovascular system. The system utilizes a pressure transducer implanted together with the pacemaker, the transducer is preferably located on the proximal axillary artery. The system features quick response based on physiological need, and also includes a reset feature which maintains a normal resting heart rate despite long term changes in blood pressure.

22 Claims, 3 Drawing Sheets

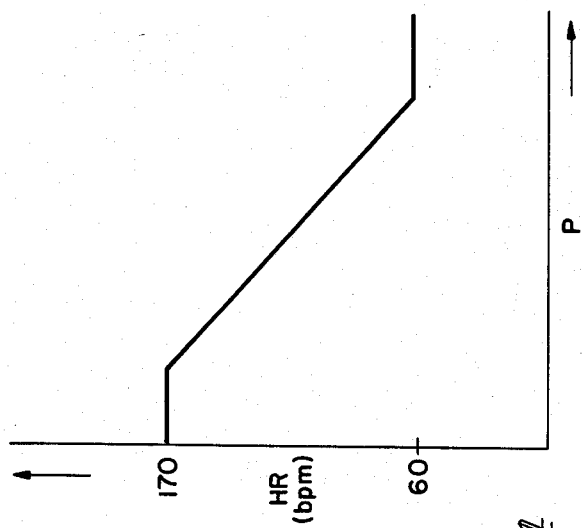
Fig. 3
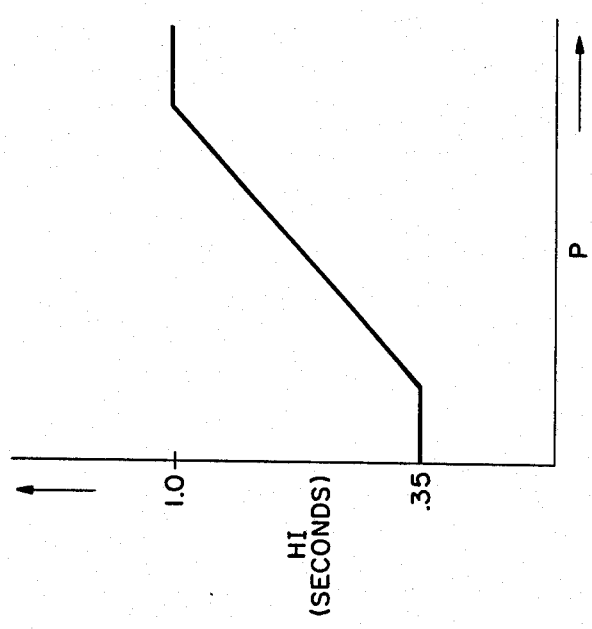
Fig. 4
Fig. 6

DEMAND PACEMAKER USING AN ARTIFICIAL BARORECEPTOR REFLEX

BACKGROUND OF THE INVENTION

Field of the Invention

The present invention relates generally to a rate responsive cardiac pacemaker, and more particularly to a pacemaker having a variable rate which is responsive to arterial pressure, thereby causing the cardiac rate to closely mimic the natural baroreceptor reflex response pattern of the heart to changing physiological need.

The cardiac pacemaker is perhaps one of the best known electronic marvels of modern medicine, and the implantation of a pacemaker in a patient has become almost a routine operation. The small, electronic device pulses the heart of the patient continuously over an extended period of time, or, in the case of demand pacemakers, monitors the heart's natural operation and provides stimulating pulses only when the the heart skips a beat. Pacemakers allow patients with heart problems which would have been either fatal or incapacitating without a pacemaker to resume relatively normal lives.

It will be realized by those skilled in the art that the modern pacemaker is a highly complex device, capable of event sensing, two-way telemetry, and sensing and pacing in either or both of the atrium and the ventricle of the heart. Such pacemakers may be finely tuned by the physician subsequent to implant, and the parameters tweaked to result in optimum pacing performance.

Despite the impressive sophistication of such pacemakers, they represent a compromise due to a single major difference between the healthy heart and a paced heart- namely the response to activity, exercise, or stress. A healthy heart is rate responsive to a number of factors including physical activity or exercise. Variations in the cardiac stroke volume and systemic vascular resistance occur in the cardiovascular system due to physiological stresses such as exercise, temperature changes, postural changes, emotion, hypoglycemia, Valsalva maneuvers, etc.

To maintain adequate perfusion pressure and cardiac output under these stresses, it is necessary to adjust heart rate. The healthy heart may beat at 60 or fewer beats per minute during repose or sleep, and at 120 or more beats per minute during strenuous exercise, for example. The heart paced by a pacemaker which is non-rate responsive will typically beat at a constant rate of approximately 70 beats per minute.

It will be appreciated that the paced heart will supply more blood than is needed during sleep, and may even prevent the patient from sleeping restfully. Even more seriously, patients paced at 70 beats per minute experience substantial difficulty in engaging in strenuous activity. A moderate level of activity such as walking will cause difficulty in some patients. It is apparent that a pacemaker which varies in response to physiological need represents a highly desirable device which will enable a normal active life for patients requiring a pacemaker.

Physiological responsive cardiac pacing must optimize cardiac rate to the level of metabolic need in the absence of normal variable cardiac rate. The simplest answer to this problem is atrial tracking pacing, where the patient has a full or partial AV block and a dual chamber pacemaker pulses the ventricle in response to normal cardiac activity sensed in the atrium. However, this technique is not possible in many patients with sinus bradycardia or atrial fibrillation, and so rate responsive pacing is necessary to mimic the normal variable cardiac rate.

A variety of physiological responsive pacing systems have been proposed, with the systems using a variety of physiological parameters as the basis for varying cardiac rate. These parameters include blood temperature, various sensed timing signals from the heart, blood chemistry, respiratory rate, nervous system activity, physical activity, and pressure measured within the heart at various locations. These systems will be discussed briefly below, and the problems inherent in each of the systems will become evident.

Venous blood temperature is measured in the right ventricle by Cook et al. in U.S. Pat. No. 4,436,092. Since blood temperature has been found to rise during exercise and the corresponding body core temperature increase, blood temperature indicates greater physiological need for blood supply. However, the response of such a system in quite slow. In addition, the system is inexact due to the coarseness at which measurements may be taken, the ingestion of cold liquids, and the effect caused by presence of a fever.

Both the QT interval and the P wave have been used to vary heart rate. The use of the QT interval is discussed in U.S. Pat. No. 4,228,803, to Rickards, and involves detection of the repolarization T wave subsequent to pacemaker stimulation (indicating the Q wave). A shorter QT interval is used to produce a higher paced cardiac rate. This system is slow in response, and not highly specific due to variations caused both by drugs ingested and by the used of pacemaker stimulation rather than using sensed contractions.

The use of the P wave is taught in U.S. Pat. No. 4,313,442, to Knudson et al. By responding to average atrial rate through detection of the P wave, the system varies cardiac rate. This is little more than a dual chamber system, and, as mentioned above, this technique is not possible in many patients with sinus bradycardia or atrial fibrillation. It is also slow due to time averaging, and possibly subject to errors due to faulty signal detection which could drive the heart at a greater that desired rate.

Blood chemistry sensors may detect oxygen saturation or blood pH. The use of oxygen saturation is shown in U.S. Pat. No. 4,202,339, to Wirtzfeld et al., and in U.S. Pat. No. 4,467,807, to Bornzin. An optical detector is used to measure the mixed venous oxygen saturation, typically in the right ventricle. A diminution in the mixed venous oxygen saturation is used to produce a higher paced cardiac rate. The speed of this system is also quite slow, and sensor reliability and life are not yet great enough to produce a very reliable product.

The use of pH sensing is taught in U.S. Pat. No. 4,009,721, to Alcidi, and in U.S. Pat. No. 4,252,124, to Mauer et al. A membrane pH sensor electrode is typically placed in the right ventricle, and senses pH, which is proportional to the blood concentration of carbon dioxide, which is generated in increasing amounts by exercise. A diminution in the pH level is used to produce a higher paced cardiac rate. The speed of this system is slow, and sensor reliability over an extended lifetime is not yet great enough to produce a reliable product.

A respiratory rate sensor is shown in U.S. Pat. No. 3,593,718, to Krasner. An increase in respiratory rate causes a the system to produce a higher paced cardiac rate. Cardiac rate does not exactly track respiratory rate in the normal heart, and the problem with the Krasner device is that it is either too slow if respiratory rate is time-averaged, or it may be too fast if instantaneous respiratory rate is used. In addition, the system uses variations in chest impedance to produce a signal, making it both subject to false signals due to a variety of causes including loose sensors, and highly subject to damage from defibrillation.

Activities of the central nervous system are highly relevant to modification of cardiac rate. One use of nerve impulses is detailed in U. S. Pat. No. 4,201,219, to Bozal Gonzales, in which a neurodetector device is used to generate electrical signals indicative of nerve impulses. The frequency of the impulses is utilized to modify the paced cardiac rate. The implementation of this is considerably difficult, in that a stable, predictable coupling to the Hering nerve is required. In addition, it is difficult to discriminate between the signals detected to obtain the single signal desired, in that the technology involved is still in its infancy. This approach, while probably having a fast response, thus has neither the sensor reliability nor the system specificity necessary for a reliable product.

The approach which has found its way into the first generation of commercially available pacemakers is the activity sensing variable rate device, which varies rate in response to body movement. As body movement increases, so does the output from the sensor, typically a piezoelectric device producing an electrical output in response to vibratory movement induced by body movement. Increasing output from the sensor causes the system to produce a higher paced cardiac rate. Examples of such devices are illustrated in U.S. Pat. No. 4,140,132, to Dahl, and in U.S. Pat. No. 4,428,378, to Anderson et al.

Activity sensing variable rate pacemakers have a fast response and good sensor reliability. However, they are less than ideal in system specificity. For example, if a person with such a pacemaker was restfully riding in a car on a very bumpy road, his heart rate would increase dramatically at a time when such an increase was not warranted, and, indeed, would not be initiated by the normal healthy heart. Similarly, if the person was pedaling at a furious rate on an exercise bicycle while his upper body were relatively motionless, he would likely run out of oxygen and pass out. Despite the commercial implementation of such devices, it will therefore be appreciated that they are far from perfect.

The last approach which has been taken is to use the pressure of blood to determine an appropriate heart rate. Using blood pressure within the heart to regulate heart rate has been the basis for several proposed systems, beginning with the system shown in U.S. Pat. No. 3,358,690, to Cohen. Cohen uses a pressure sensor in the atrium to detect a high pressure condition, and, after a short delay, provides a pacing pulse to the ventricle. This system also assumes that the atrium is operating completely normally, and thus it is not possible to use this system in many patients with sinus bradycardia or atrial fibrillation.

U.S. Pat. No. 3,857,399, to Zacouto, teaches a system that measures either left ventricle pressure or intramyocardial pressure using a sensor located in the left ventricle. This is absolutely unacceptable, since to introduce a sensor through the interventricular septum would be dangerous to say the least. Likewise, a cutdown or percutaneous introduction of such a sensor into the heart through an artery would result in necrosis of the artery.

U.S. Pat. No. 4,566,456, to Koning et al., uses a pressure sensor in the right ventricle, and, in response to either the pressure sensed or the time derivative of pressure sensed, provides a pacing pulse to the right ventricle. This system also assumes that the atrium is operating completely normally, and so it is not possible to use this system in many patients with sinus bradycardia or atrial fibrillation.

Finally, U.S. Pat. No. 4,600,017, to Schroeppel, teaches the use of a pressure sensor in the right ventricle to sense the closing of the tricuspid valve, and provides a pacing pulse thereafter. Once again, if the atrium is not operating completely normally it is not possible to use this system.

It may therefore be appreciated that there exists a substantial need for a physiological response variable rate pacemaker which has the desirable features of fast response, long term reliability, and high specificity. The fast response of the system insures that the heart rate will be varied according to current demand, not the demand of some previous time averaged period. Long term reliability is of course needed in order to make the device suitable for human implant. Finally the system must respond at times when a response is appropriate, and not respond when a response is not appropriate. This combination of objectives must of course be achieved with no relative disadvantage.

SUMMARY OF THE INVENTION

The disadvantages and limitations of the background art discussed above are overcome by the present invention. With this invention, blood pressure is used to regulate heart rate. It has been known for some time that an inverse relationship exists between blood pressure and heart rate, and that the baroreceptor reflex, which is the blood pressure control system of the body, causes changes in cardiac rate to provide short term control of blood pressure.

The invention is an artificial pacemaker system which in the preferred embodiment adjusts heart rate using a microprocessor-based method that is similar to the human body's natural baroreceptor reflex. (It will be apparent to those skilled in the art that other circuits could be utilized instead of a microprocessor-based circuit without departing from the spirit of the present invention.) In the system of the present invention, arterial blood pressure is measured by a transducer which is preferably extravascular and located at an easily accessible artery such as the proximal axillary artery. A first embodiment of the invention uses a feedback type system having a relatively fast response feedback loop which adjusts heart rate, within minimum and maximum limits, quickly, with a response time of a few seconds. The preferred embodiment of the present invention also has this first fast feedback loop to adjust heart rate quickly, and also has a second relatively slow feedback loop which tends to maintain resting heart rate at a nominal value over an extended period of time.

The fast loop is designed based on physiological investigations of the baroreceptor reflex that has shown a linear relationship between heart interval (the reciprocal of heart rate) and arterial pressure. The feedback signal used in the fast loop of the preferred embodiment is the mean arterial pressure, due to its ease of measurement, low noise, lower frequencies, ease of calibration, and insensitivity to systolic pulse amplification due to pressure wave reflections in the arterial network. Using mean arterial pressure also provides the system with a fast response time, and a relatively high degree of system specificity.

This second or slow loop is an electrical analog of the baroreceptor reset mechanism, and it accounts for long term changes in sensed blood pressure levels of the patient, such as those caused by hypertension or by drift in the output of the pressure transducer. The slow loop of the preferred embodiment has a response time of hours or days, whereas the fast loop has a response time of seconds.

Implementation of the preferred embodiment utilizes an extravascular arterial blood pressure transducer on the proximal axillary artery. The pressure signal may be low pass filtered, and then sampled using an A/D converter. The microprocessor then computes the desired heart interval or heart rate based on the sampled blood pressure and other parameters.

The microprocessor would then output this heart rate to a stimulator circuit, which is entirely conventional. Parameters set by the physician using telemetry would include sensitivity (gain of the fast feedback loop), intercept (a constant which may be used together with the sensitivity value in the control equation to determine the nominal resting heart rate), minimum and maximum heart rate, calibration constants, as well as the usual pacemaker parameters. Telemetry may be used for calibration and for monitoring blood pressure, heart rate, and set parameters.

It may thus be appreciated that the invention enables a system having distinct advantages over previously existing variable rate pacing systems. The system has the most important characteristic of a fast response to physiological need, making it closely follow the operation of a normal healthy heart. The system features a high degree of specificity, unlike most of the previously known systems. In addition, the present invention is highly reliable, and will operate over an extended lifetime. The system of the present invention achieves these advantages without incurring any relative disadvantage, making it a highly desirable and marketable device.

DESCRIPTION OF THE DRAWINGS

These and other advantages of the present invention are best understood with reference to the drawings, in which:

FIG. 4 is a graph approximating the linear portion of heart rate as a function of arterial pressure;

FIG. 5 is a block diagram of the basic operation of the system of the present invention; and FIG. 6 is a block diagram of the operation of the preferred embodiment of the present invention, in which the system shown in FIG. 3 is modified to maintain resting heart rate at a nominal value.

DETAILED DESCRIPTION OF THE PREFERRED EMBODIMENT

Figure 1:
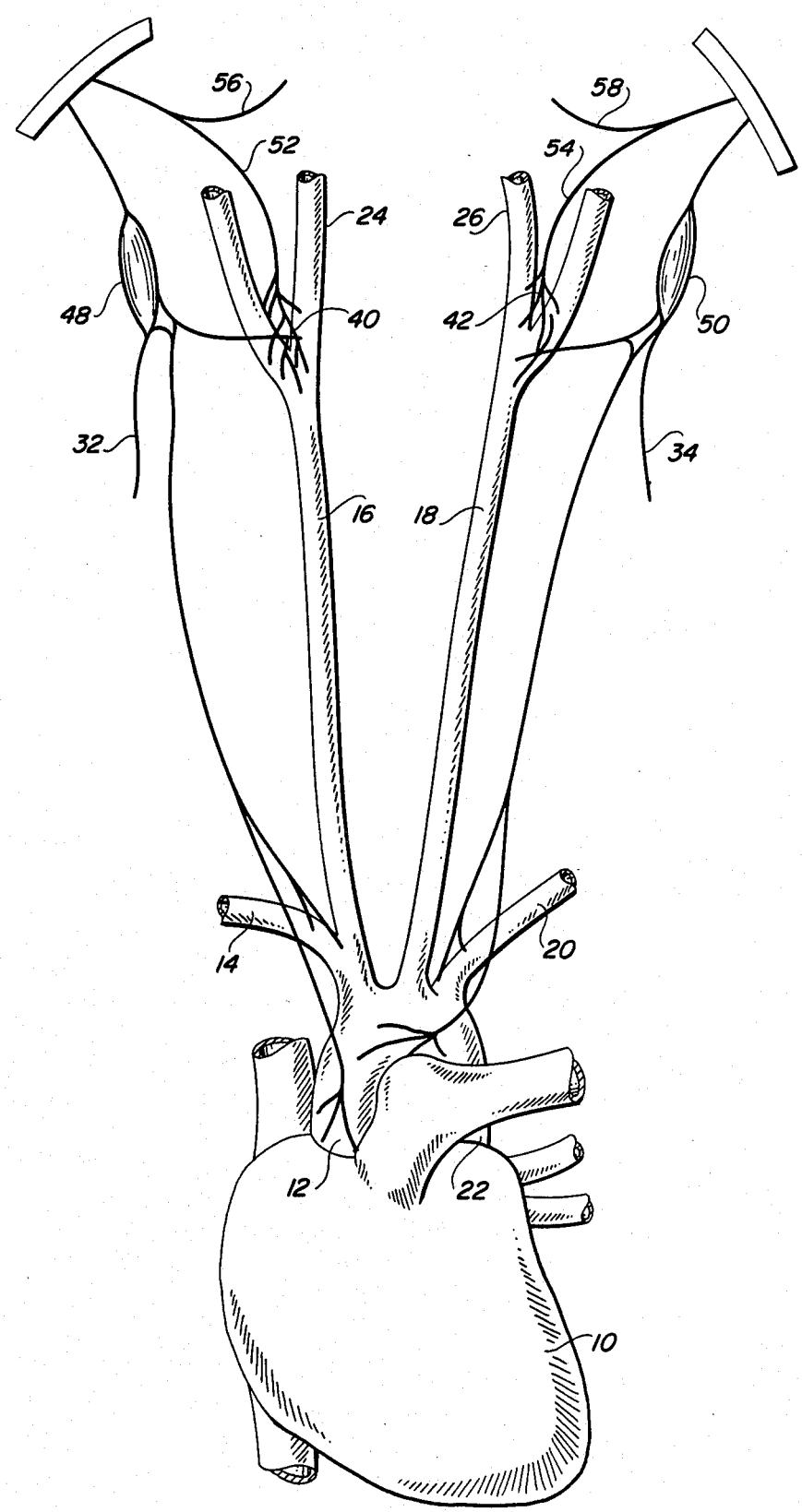
FIG. 1 is a diagramatic illustration of the natural stretch baroreceptors of a human being, showing the innervation of the carotid sinus and the aortic arch.

Before discussing the preferred embodiment of the present invention, it is helpful to briefly discuss the natural baroreceptor heart rate control system, which is shown in FIG. 1. The heart 10 pumps oxygenated blood out through the aortic arch 12, which leads to the right subclavian artery 14, the right common carotid 16, the left common carotid 18, the left subclavian artery 20, and the thoracic aorta 22. The body's system utilizes stretch receptors located in arterial walls in the aortic arch 12 and at the bifurcation of the carotid arteries 16, 18 in the carotid sinus portion of the neck. The bifurcation of the carotid arteries 16, 18 leads to exterior carotid arteries 24, 26, respectively, and to interior carotid arteries 28, 30, respectively.

Nerve fibers extending from stretch receptors in the aortic arch 12 join the left and right vagus nerves 32, 34, respectively, with these fibers being referred to as cardiac depressor nerves 36, 38. A number of nerves extend from the stretch receptors at the bifurcation of the carotid arteries 16, 18 in the carotid sinus, with the areas immediately above the bifurcations being referred to as the carotid bodies 40, 42. Nerve branches 44, 46 extending from the carotid bodies 40, 42, respectively, join the ganglions of vagus 48, 50, respectively. Other nerve fibers comprising the sinus nerve branches 52, 54 (generally referred to as "Hering's nerves") of the glossopharyngeal nerves 56, 58, respectively, also extend from the carotid bodies 40, 42, respectively, to the medulla (not shown).

Although the exact mechanism by which the body controls the heart rate in response to blood pressure is not well understood, it is known that nerve signals are generated in response to distortion, which varies in direct response to varying arterial blood pressure. Nerve pulses are generated at pressures typically above 50 mmHg, and occur at ever-increasing frequency until blood pressure reaches approximately 170 mmHg. Heart rate varies inversely with the frequency of the nerve impulses. The slope of the relationship between nerve impulse frequency as a function of carotid sinus pressure is greatest at the normal level of mean arterial pressure, which means that the body's system responds most effectively when blood pressure is within a normal range.

Figure 2:
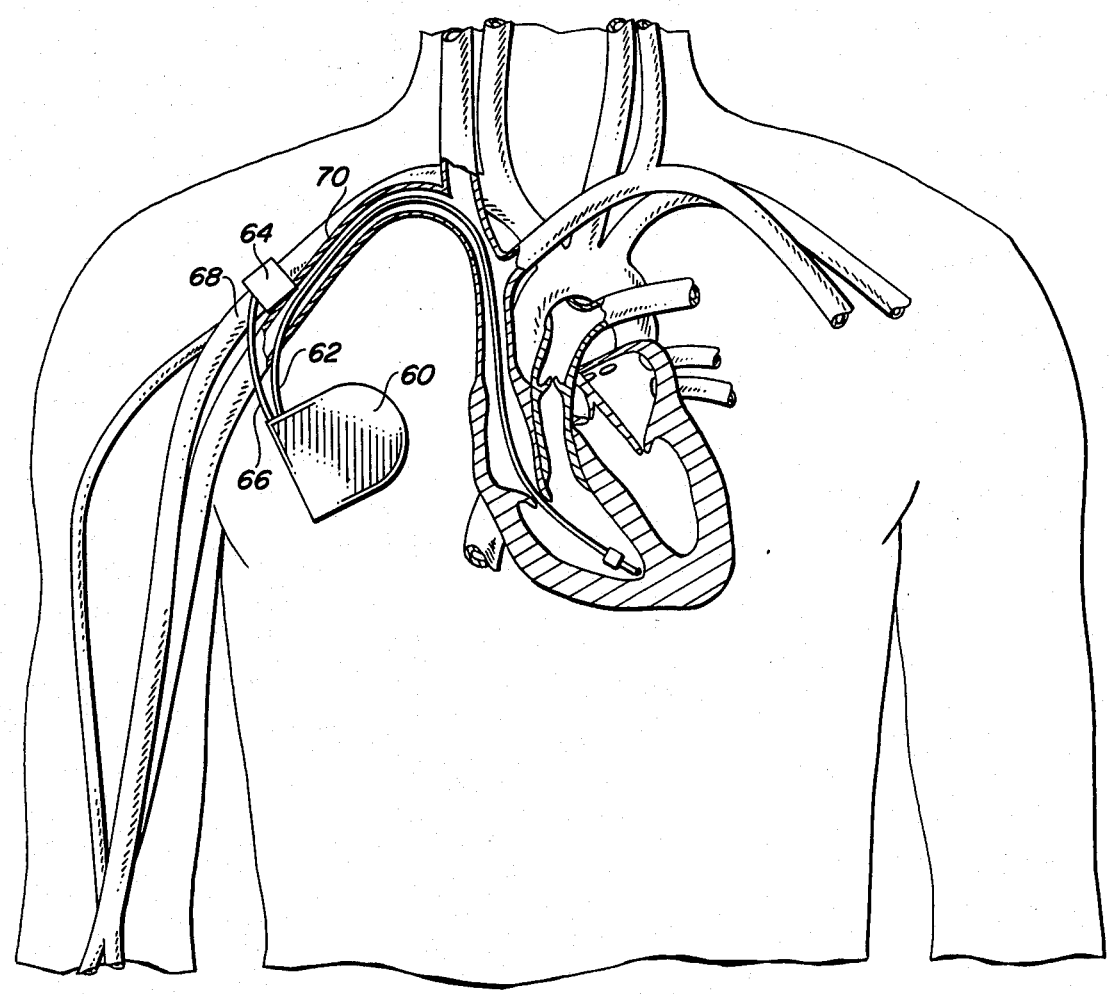
FIG. 2 is a diagramatic illustration of the installation of the system of the present invention in the abdominal region of a human being.

The system of the present invention mimics the body's natural response by controlling heart rate in response to arterial blood pressure. As shown in FIG. 2, the present invention has three components: an electronic pulse generator 60, a pacing lead 62 implanted in a vein leading to the heart, and a pressure sensor 64 connected to the pulse generator 60 by a lead 66. In FIG. 2, the pulse generator is shown implanted in the right upper chest cavity. As is the case with a conventional pacemaker, the pulse generator 60 could be implanted in either side of the body.

The lead 62 illustrated in FIG. 2 is a bipolar ventricular lead, although the system could also utilize a unipolar lead, or even an atrial lead in some instances. Likewise, in the case of a few prospective recipients, it may be even desirable to use a dual chamber pacemaker system. It will be appreciated by those skilled in the art that the pacemaker technology used in the present invention is entirely standard with the exception of the components utilized to provide a variable rate command to the pacing circuitry.

The pressure sensor 64 is used to monitor the pressure in an easily accessible artery such as the proximal axillary artery 68. Any artery which is relatively close to the heart may be used, with the proximal axillary artery 68 being the preferred artery due to its location. Since the preferred location to implant the pulse generator 60 is the location shown in FIG. 2 (although on either side of the chest), it is desirable to use an artery which is easily accessible through the incision used to implant the lead 62 and the pulse generator 60. The proximal axillary artery meets these requirements. Only a short distance away and even closer to the heart, the subclavian artery 70 may also be used, although it is less convenient to use the subclavian artery 70.

The pressure sensor 64 used must be located external to the artery, since placing a transducer within the artery would likely lead to necrosis of the artery. The transducer may sense the stretch in the arterial wall caused by pressure change of blood within the artery and thereby produce a variable output indicative of or proportional to arterial pressure, much the same as the body's natural method of response. The pressure sensor 64 may operate by surrounding the artery and detecting pressure change with a strain detector device. Such pressure sensors are described in "Implantable Sensors for Closed-Loop Prosthetic Systems," Edited by Wen H. Ko, Futura Publishing Co., Inc., (New York, 1985), on pages 35-88. Alternatively, the pressure sensor 64 may measure pulse transit time, which is indicative of arterial pressure.

Figure 3:
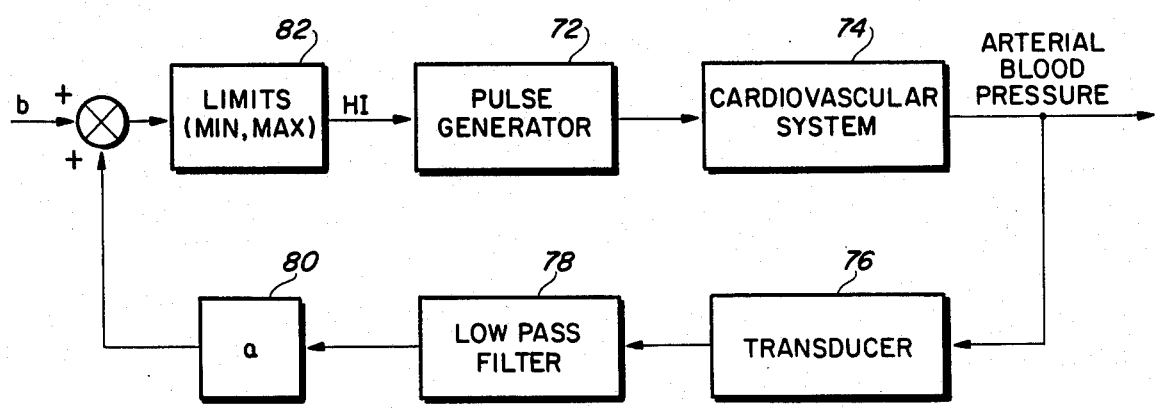
FIG. 3 is a graph approximating the linear portion of heart interval as a function of arterial pressure.

FIG. 3 illustrates a linear approximation of the relationship between heart interval (the reciprocal of heart rate) and arterial pressure. Between the minimum and maximum limits, the relationship may be expressed as a linear regression:

$$HI = a \cdot P + b \quad (1)$$

where HI is heart interval, P is arterial pressure, a is slope, and b is the HI axis intercept. See also "Comparison of the Reflex Heart Response to Rising and Falling Arterial Pressure in Man," T. G. Pickering, B. Gribbin, and P. Sleight, *Cardiovascular Research*, Vol. 6, pp. 277-283 (1972). It will of course be realized by those skilled in the art that the parameters a and b may vary from individual to individual, and will also be dependent on the measurement of arterial pressure. In the graph, HI typically has a range of values between 0.35 seconds and 1 second.

Likewise, FIG. 4 depicts the same approximated linear relationship (using a Taylor series approximation), but with heart rate graphed as a function of arterial pressure. Between the minimum and maximum limits, the relationship may be expressed as a linear regression:

$$HR = c \cdot P + d \quad (2)$$

where HR is heart rate, P is arterial pressure, c is slope, and d is the HR axis intercept. In the graph, HR typically has a range of values between 60 beats per second and 170 beats per second.

The linear relationship describing FIG. 3 and expressed in equation 1 may be used to set up a proportional control loop, as shown in FIG. 5. The system shown in FIG. 5 illustrates in simplified fashion the operation of the system of the present invention used to control the frequency of the stimulus supplied by the pulse generator 60 (FIG. 2) to the heart. A pulse generator 72 paces the heart (not shown) to pump blood throughout the cardiovascular system 74. An output of the cardiovascular system 74 is arterial blood pressure, which is monitored by a transducer 76 which produces an electrical output proportional to arterial blood pressure.

An error which could be introduced into the system at this point is peak amplification of the arterial wave occurring as a result of reflections in the arterial network (such as those occurring of bifurcations in the arteries). Another closely related error is high noise content of systolic arterial pressure due to the peak detection method of measurement, and also the inherent variability in the signal from one heartbeat to the next. It is therefore advantageous to use mean pressure, which is smoother, has less noise, is not subject to peak amplification, and is in fact easier to measure.

Measurement of mean pressure may be made by filtering the output of the transducer 76 through a low pass filter 78. A suitable low pass filter is, for example, a second or third order filter (a Butterworth filter would work well) with a time constant of approximately 0.3 seconds to 1.6 seconds. Such a filter would have a cutoff frequency between approximately 0.1 Hz to 0.5 Hz. The tradeoff involved in selecting a cutoff frequency is that while lower cutoff frequencies minimize harmonics due to the pulsatile nature of the arterial pressure waveform, such lower frequencies also introduce more phase shift into the feedback loop and make the system less stable.

The mean pressure signal output from the low pass filter 78 is supplied to an amplifier 80, in which a gain of a is provided. The output of the amplifier a is then added to the constant input b and the summed signal is provided to a limiting device 82. The limiting device 82 will output the summed signal input to it, except when the summed signal is below a minimum value (for example, 0.35 seconds as shown in the graph of FIG. 3) or above a maximum value (for example, 1.0 second as shown in the graph of FIG. 3). In such cases where the summed signal exceeds these limits, the limiting device 82 will output the limit of the value.

The output of the limiting device 82 is HI, and it is supplied to the pulse generator 72. The pulse generator 72 will then pace the heart at a rate which is the reciprocal of HI. Of course, as is well known in the art, the pulse generator 72 may operate as a demand pacer, pacing the heart only when the natural rate does not meet the calculated rate. Also, the pulse generator will have other inputs, all of which are well known in the art. The variables a and b are set by the physician to provide the desired response, and the minimum and maximum values of the limiting device 82 may also be set by the physician in the preferred embodiment. All such settings may be made by two way telemetry, as is known in the art.

It will also be appreciated by those skilled in the art that the system shown in FIG. 5 may be modified to utilize equation 2 above and reflect the control shown in FIG. 4, by substituting c and d for a and b, respectively, and by using the limits shown in FIG. 4 rather than those of FIG. 3. Such limits on HR are typically between 60 and 170 beats per second. In this case, the limiting device supplies HR to the pulse generator rather than HI.

It will be realized by those skilled in the art that since a microprocessor is used in the preferred embodiment to implement the control scheme, the relationship between blood pressure and HR (or HI) need not be a linear approximation, but rather could be a nonlinear transfer function. By utilizing this approach, the system may be made to simulate the normal healthy response even more closely.

The system discussed to this point in conjunction with FIG. 5 is a fast acting system which varies heart rate as a function of arterial pressure. This system has a disadvantage in that it has no means for keeping the resting heart rate at a preset level. For example, if an individuals blood pressure changes over a relatively long period of time, the system of FIG. 5 would also change the individual's resting heart rate. The practical effect of this is that with elevated blood pressure, the heart rate would remain low even when the physiological demands of the body were relatively high. In any case, the system would no longer closely mimic the normal functions of the body.

The system of FIG. 5 may be modified to overcome this problem, as shown in FIG. 6. FIG. 6 operates the same as FIG. 5 with a single exception- the fixed value b is replaced with a variable b' which functions to maintain resting heart rate at a consistent value over an extended period of time. The desired resting heart rate RHR is supplied to a reciprocal function device 84, which has as its output the desired heart interval RHI. The output of the limiting device 82, which is heart interval HI, is subtracted from RHI, the desired resting heart interval, to produce an instantaneous error signal which is supplied to a reset controller 86. (Note that if the system models equation 2 and FIG. 4, the output of the limiting device 82 would be HR, and the reciprocal function device 84 would not not be needed to obtain RHI.)

The reset controller would function over an extended time period, on a scale of days to weeks. It functions to assure that in the long term, resting heart rate remains constant. The response is closed loop, and preferably includes nonlinearities to ensure safety. The reset controller 86 may be, for example, a proportional or proportional-plus-integral controller with nonlinearities, or it may alternatively utilize lead-lag or pole-placement to accomplish the reset function. This system resets the intercept b' of the linear function, while maintaining the slope a, and has the effect of moving the linear transfer function shown in FIG. 3 up or down.

It may also be desirable to adjust the slope a, and this is within the contemplation of the present invention. It would require only an additional control line from the reset controller 86 to the amplifier 80 to control gain a'. It also may be desirable to limit either or both of a' and b' within a range, but such limits constitute fine tuning of a degree which does not need to be specifically addressed herein, but which will be readily apparent to those skilled in the art.

It will be apparent to those skilled in the art that the electronics of the system described above are easily attainable using available technology. The electronics may be contained in the same case as the pulse generator and a power source, and therefore may use the same telemetry, power, and control systems.

It will thus be appreciated that the present invention as described above defines a system having distinct advantages over previously existing variable rate pacing systems. The system has a fast response to physiological need, and it closely follow the operation of a normal healthy heart, while maintaining a desired resting heart rate. The system features a high degree of specificity, unlike previously known systems. In addition, it is highly reliable while remaining relatively simple to implant, and will operate over an extended lifetime. The system of the present invention achieves all of these advantages without incurring any relative disadvantage, therefore making it a highly desirable improvement in the state of the art.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. A cardiac pacemaker for stimulating a heart to beat at a rate which is variable in response to physiological need, comprising:
   a pulse generator for generating periodic electrical pulses at a rate determined by a rate input signal supplied to said pulse generator;
   a pacing lead for delivering said periodic electrical pulse generated by said pulse generator to said heart;
   means for sensing arterial blood pressure and generating a signal indicative of arterial blood pressure; and
   means for generating said rate input signal in response to said signal indicative of arterial blood pressure.

2. A cardiac pacemaker as defined in claim 1, wherein said pulse generator generates said periodic electrical pulses only in the absence of naturally occurring heartbeats.

3. A cardiac pacemaker as defined in claim 1, wherein said sensing means senses arterial blood pressure at the proximal axillary artery.

4. A cardiac pacemaker as defined in claim 2, wherein said sensing means is located externally of the proximal axillary artery.

5. A cardiac pacemaker as defined in claim 1, wherein said sensing means comprises:
   a transducer located externally about an artery for producing a variable output indicative of the stretch in the arterial wall caused by pressure change of blood within said artery.

6. A cardiac pacemaker as defined in claim 5, wherein said transducer is a strain detector device.

7. A cardiac pacemaker as defined in claim 5, wherein said transducer operates by measuring pulse transit time.

8. A cardiac pacemaker as defined in claim 1, wherein said generating means has as an input the signal generated by said sensing means, said generating means using a transfer function to produce said rate input signal in response to said signal generated by said sensing means.

9. A cardiac pacemaker as defined in claim 8, wherein said transfer function is nonlinear.

10. A cardiac pacemaker as defined in claim 8, wherein said transfer function is linear.

11. A cardiac pacemaker as defined in claim 10, wherein said rate input signal is commanded heart interval, and said transfer function produces a value of commanded heart interval which is equal to a first constant a times the signal indicative of arterial pressure, plus a second constant b.

12. A cardiac pacemaker as defined in claim 10, wherein said rate input signal is commanded heart rate, and said transfer function produces a value of commanded heart rate which is equal to a third constant c times the signal indicative of arterial pressure, plus a fourth constant d.

13. A cardiac pacemaker as defined in claim 1, wherein said generating means comprises:
   means for amplifying the signal indicative of arterial blood pressure, said amplifying means having a gain a and producing an amplified output; and
   means for summing said amplified output with a constant b to produce said rate input signal.

14. A cardiac pacemaker as defined in claim 13, additionally comprising:
   means for maintaining the long term resting heart rate at a predetermined rate.

15. A cardiac pacemaker as defined in claim 14, wherein said maintaining means comprises:
   means for generating an error signal between said predetermined rate and said rate input signal; and
   means for periodically resetting said constant b in response to said error signal.

16. A cardiac pacemaker as defined in claim 13, additionally comprising:
   means for filtering said signal indicative of blood pressure to minimize harmonics due to the pulsatile nature of the arterial pressure waveform.

17. A cardiac pacemaker as defined in claim 16, wherein said filtering means has a time constant of between 0.3 and 1.6 seconds.

18. A cardiac pacemaker as defined in claim 1, wherein said generating means produces a rate input signal corresponding to a heart rate of between 60 and 170 beats per minute.

19. A cardiac pacemaker as defined in claim 1, additionally comprising:
   means for maintaining the long term resting heart rate at a predetermined level.

20. A cardiac pacemaker for stimulating a heart to beat at a rate which is variable in response to physiological need, comprising:
   a pulse generator for generating periodic electrical pulses at a rate determined by a rate input signal supplied to said pulse generator;
   a pacing lead for delivering said periodic electrical pulse generated by said pulse generator to said heart;
   a transducer located about an artery for producing a variable output signal indicative of arterial blood pressure in response to the stretch in the arterial wall caused by pressure change of blood within said artery;
   means for amplifying the signal indicative of arterial blood pressure, said amplifying means having a gain a and producing an amplified output; and
   means for summing said amplified output with a constant b to produce said rate input signal.

21. A cardiac pacemaker for stimulating a heart to beat at a rate which is variable in response to physiological need, comprising:
   a pulse generator for generating periodic electrical pulses at a rate determined by a rate input signal supplied to said pulse generator;
   a pacing lead for delivering said periodic electrical pulse generated by said pulse generator to said heart;
   a transducer located about an artery for producing a variable output signal indicative of arterial blood pressure in response to the stretch in the arterial wall caused by pressure change of blood within said artery;
   means for amplifying the signal indicative of arterial blood pressure, said amplifying means having a gain a and producing an amplified output;
   means for summing said amplified output with a constant b to produce said rate input signal; and
   means for maintaining the long term resting heart rate at a predetermined rate.

22. A method of stimulating a heart to beat at a rate which is variable in response to physiological need, comprising:
   sensing arterial blood pressure and generating a signal indicative of arterial blood pressure;
   generating said rate input signal in response to said signal indicative of arterial blood pressure;
   generating periodic electrical pulses at a rate determined by a rate input signal; and
   delivering said periodically generated electrical pulse to said heart.

* * * * *